United States Patent [19]

Fry

[11] Plant 4,772

[45] * Oct. 6, 1981

[54] MUSCADINE GRAPE

[76] Inventor: Byard O. Fry, 612 Terrace St., Griffin, Ga. 30223

[ * ] Notice: The portion of the term of this patent subsequent to Oct. 6, 1998, has been disclaimed.

[21] Appl. No.: 701,792

[22] Filed: Jul. 1, 1976

[51] Int. Cl.[3] ..... A01H 5/03

[52] U.S. Cl. ..... Plt./47

[58] Field of Search ..... Plt./47

*Primary Examiner*—Robert E. Bagwill

*Attorney, Agent, or Firm*—Stanley L. Tate

[57] ABSTRACT

A new variety of muscadine which is very vigorous, with large fruit of a light greyed orange color which occurs in large clusters of 10 to 25 berries, each berry having a diameter of about 0.9 inches; the individual berries having a sugar content of from about 18.50 to about 22.00 percent and producing a fruit yield of about four (4) tons per acre.

1 Drawing Figure

DESCRIPTION OF THE VARIETY

The new and distinct variety of muscadine grape which is the subject of the present application was originated by crossing the unnamed seedling 44-6 with the unnamed seedling 44-7, the former being the seed parent and the latter being the pollen parent.

The general objective of the breeding was to produce an improved variety of muscadine having a bright light greyed orange fruit, relatively high fruit yield per acre, and high average individual berry sugar content described and claimed herein meets all of the aforesaid requirements, all of which distinguish it from its parents as well as from all other varieties of muscadine of which the applicant is aware.

In comparison with both the seed parent and the pollen parent, the new variety produces a sweeter fruit. The fruit color of the new variety is a light bright greyed orange shade which has not previously been observed in either parent or in other muscadine varieties. The average individual berry sugar content of this new variety ranges from about 18.5 percent to about 22.00 percent as compared to the sugar content of both parents which ranges from about 17.00 percent to about 19.00 percent. The fruit of the new variety ripens in very large clusters of from about 10 to 25 berries per cluster during mid-season which in Brooks, Ga., is from about September 15 to about October 15. The average crop yield of the new variety is about four (4) tons per acre a yield which is considerably higher than the yield of either parent.

Asexual reproduction of the new variety by layering as performed at Brooks, Ga., shows that the foregoing characteristics and distinctions come true to form and are established and transmitted through succeeding propagations.

The accompanying photograph shows a typical specimen of the vegetative growth and fruit of the new variety when the fruit is ripe and ready for picking and as depicted in color as nearly true as it is reasonably possible to make the same in color illustration of this character.

The following is a detailed description of the new variety.

Species: *Vitis rotundifolia.*
Type: Vine.
Seed parent: Seedling 44-6.
Pollen parent: Seedling 44-7.

Propagation: Holds its distinguishing characteristics through succeeding propagations by layering.
Locality where grown and observed: Brooks, Ga.
Fruit borne: Usually in large clusters of from 10 to 25 berries.
Fruit size: Larger than the fruit of either parent having a diameter of about 0.9 inches.
Fruit color: Greyed-orange Group 176 B-Fan 4.
Fruit maturity: September 15 to October 15 at Brooks, Ga., and depending upon seasonal conditions.
Sugar content, individual berry: 18.50 to about 22.00 percent.
Fruit shape: Uniform round.
Seeds:
- *Average diameter.*—5/32 inches.
- *Average seeds per berry.*—3.82.

Pulp color: Light green, Color Group 59A.
Consistency: Very soft, melting and very juicy when compared to other muscadine varieties.
Skin: Adheres to pulp.
Foliage:
- *Leaf color.*—Green reading 139-A on the color chart of The Royal Horticultural Society, London England.
- *Leaf size and shape.*—Similar in size and shape to leaves of other muscadine varieties.

Reproductive organs: Self fertile.
Growth:
- *Habit.*—Vine, requires support.
- *Growth.*—Very vigorous when compared to other muscadine varieties grown under similar conditions at Brooks, Ga.
- *Canes.*—Medium heavy caliper.

Disease resistance: Tolerant to black rot and soft rot as compared to other varieties under comparable cultural conditions at Brooks, Ga.

This description was made from a muscadine vine of the new variety bearing ripe fruit in late September at Brooks, Ga.

What is claimed is:

1. The new and distinct hybrid plant variety of muscadine grape as described and illustrated which is primarily distinguished as to novelty by the unique combination of very vigorous vine, large fruit of a light bright greyed orange color wherein said fruit occurs in large clusters of from about 10 to 25 berries having an individual berry diameter of about 0.9 inches, an individual berry fruit sugar content of from about 18.50 to about 22.00 percent and producing a yield of about four (4) tons per acre.

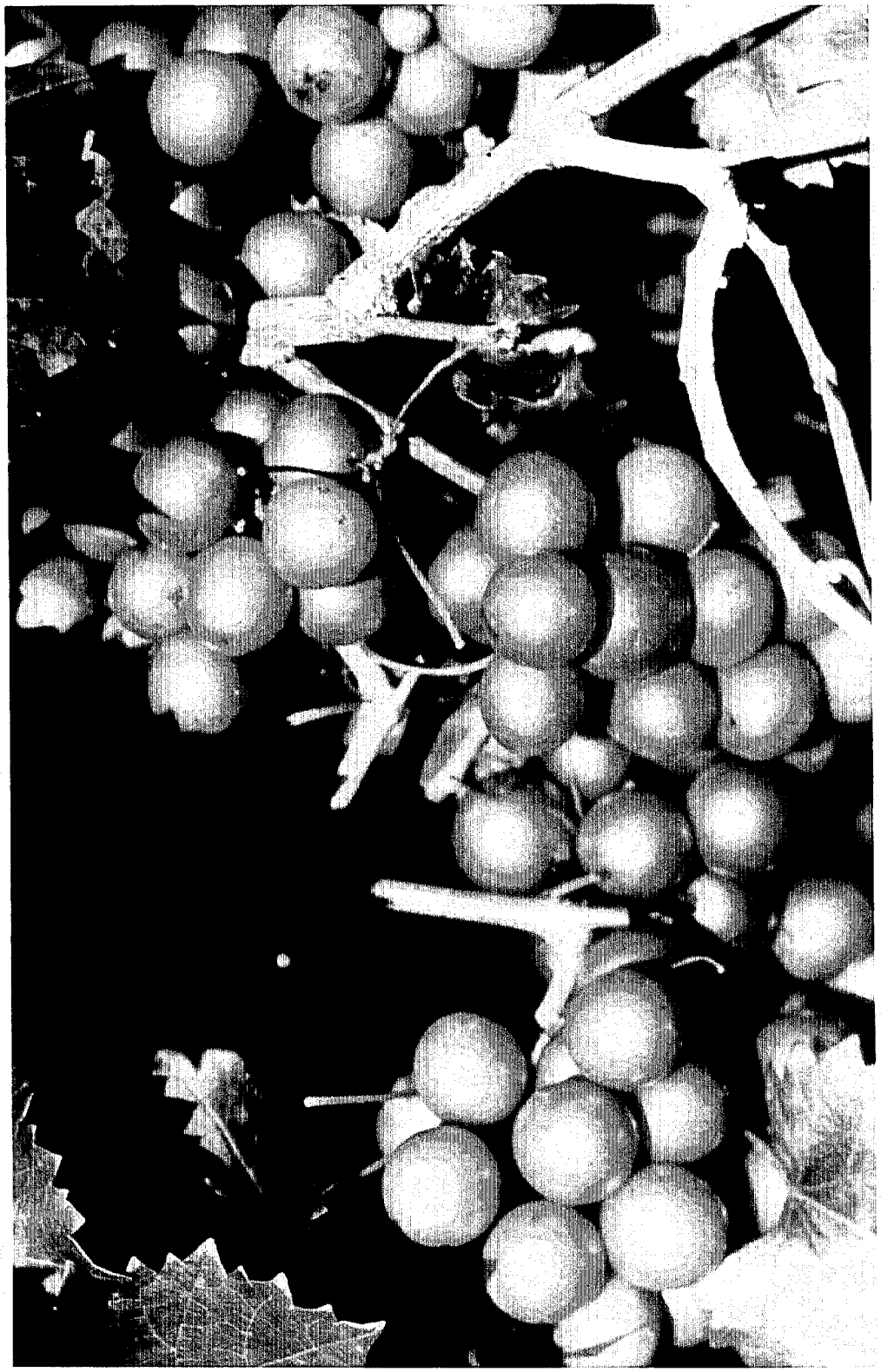

* * * * *